United States Patent
Dohi

(10) Patent No.: US 7,022,887 B2
(45) Date of Patent: Apr. 4, 2006

(54) METHOD FOR PREPARING DIARYLALKANES

(75) Inventor: Hideyuki Dohi, Yokohama (JP)

(73) Assignees: Nippon Petrochemicals Co., Ltd., Tokyo (JP); ExxonMobil Chemicals Patents Inc., Baytown, TX (US)

( * ) Notice: Subject to any disclaimer, the term of this patent is extended or adjusted under 35 U.S.C. 154(b) by 278 days.

(21) Appl. No.: 10/267,470

(22) Filed: Oct. 9, 2002

(65) Prior Publication Data

US 2003/0109763 A1   Jun. 12, 2003

(30) Foreign Application Priority Data

Oct. 15, 2001   (JP)   ............... 2001-316339

(51) Int. Cl.
*C07C 2/66*   (2006.01)
(52) U.S. Cl. .................................... 585/467
(58) Field of Classification Search ................ 585/467
See application file for complete search history.

(56) References Cited

U.S. PATENT DOCUMENTS

| | | | |
|---|---|---|---|
| 3,832,449 A | | 8/1974 | Rosinski et al. |
| 4,482,531 A | | 11/1984 | Kuehl |
| 4,552,738 A | | 11/1985 | Rubin |
| 5,073,655 A | | 12/1991 | Angevine et al. |
| 5,453,555 A | * | 9/1995 | Chang et al. ............... 585/469 |
| 5,866,733 A | | 2/1999 | Gehrer et al. |

FOREIGN PATENT DOCUMENTS

EP   0 167 232   1/1986

* cited by examiner

*Primary Examiner*—Thuan D Dang
(74) *Attorney, Agent, or Firm*—Scully, Scott, Murphy & Presser

(57) ABSTRACT

Diarylalkanes are prepared by alkylating an aromatic compound with a styrene derivative in the presence of a catalyst of specific synthetic porous crystalline material. The aromatic compound can be, for example, benzene, toluene, xylene, ethylbenzene, cumene, etc. The styrene derivative can be, for example, styrene, methylstyrene or the like.

3 Claims, 1 Drawing Sheet

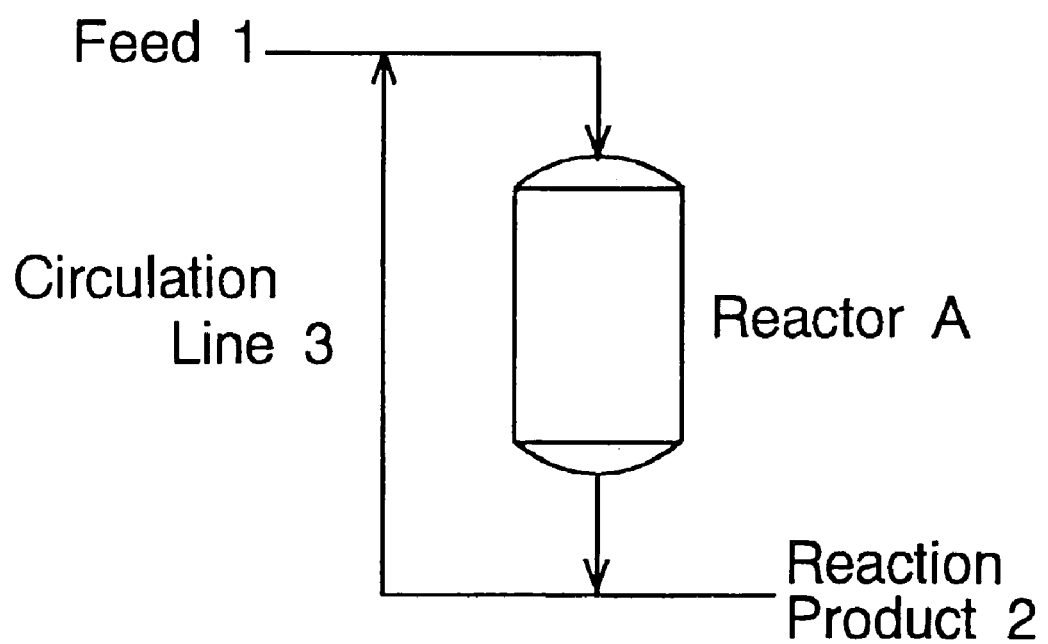

METHOD FOR PREPARING DIARYLALKANES

BACKGROUND OF THE INVENTION (1) Field of the Invention

This invention relates to an alkylation method for the preparation of diarylalkanes using a synthetic porous crystalline catalyst.

(2) Prior Art

Several methods have been proposed to react styrenes with aromatic compounds in the presence of zeolite catalysts to produce diarylalkanes, especially 1,1-diarylethane.

For example, disclosed in U.S. Pat. No. 5,073,655 is a method to alkylate benzene or the like with an alkylating agent such as styrene in the presence of a synthetic zeolite catalyst, called as MCM-22 which is characterized by an X-ray diffraction pattern.

Furthermore, in U.S. Pat. No. 5,866,733, it is disclosed that 1,1-diphenylethane is prepared by reacting benzene with styrene in the presence of a synthetic zeolite catalyst, more particularly β-zeolite, in a liquid phase or in a super critical phase.

However, in the synthetic method of this kind, there are several problems in that the selectivity for an aralkylation product is often insufficient, the conditions to attain high selectivity are difficultly adopted, or a continuous long time operation is not possible.

MEASURE TO SOLVE THE PROBLEMS

In the aralkylation of styrenes with aromatic compounds, styrene oligomers are easily produced by homo-polymerization of styrene as an accompanied reaction.

The formation of unwanted oligomers not only reduce the yield of aralkylated products but also make the separation and refining difficult, especially because the boiling points of dimers are close to, those of the intended diarylalkanes. Furthermore, compounds having an olefinic double bonds, e.g., diphenylbutenes, are contained in the dimers and the content of such impurities must be reduced as small as possible because they brings about the lowering of thermal stability and also the lowering of oxidation stability of aralkylated products and increases the offensive odor thereof.

Meanwhile, the conventionally proposed methods have not always been satisfactory in view of the above.

SUMMARY OF THE INVENTION

A method is provided herein for preparing diarylalkanes from a feedstock containing an aromatic compound and a styrene derivative. This method comprises contacting the aromatic compound and the styrene derivative under aralkylation conditions with a synthetic porous crystalline catalyst composition.

The aralkylation conditions include a temperature of from 120° C. to about 300° C., a pressure of from about 0.1 to 5 MPa, and a space velocity of from about 0.1 to 100 $(hr^{-1})$ WHSV.

BRIEF DESCRIPTION OF THE DRAWING

The drawing is a continuous flow diagram of the method of the present invention. A feed 1 continuously passes through a reactor A. A part of the reaction product 2 is circulated through the circulation line 3.

DESCRIPTION OF THE PREFERRED EMBODIMENTS

In the present invention, a catalyst composition comprising synthetic porous crystalline material having the structure of ZSM-12 is used. This catalyst and its manufacture is disclosed in U.S. Pat. Nos. 3,832,449; 4,482,531 and 4,552,738; and European Patent 167,232; the entire contents of each being incorporated herein by reference. This crystalline material is clearly distinguished from MCM-22 and β-zeolite disclosed above.

The x-ray diffraction pattern of the crystalline material ZSM-12 for use as a catalyst component in the present invention has characteristic lines shown in Table 1.

TABLE 1

| Interplanar d-Spacing (Å) | Relative Intensity $(I/I_0)$ |
|---|---|
| 11.9 ± 0.2 | M |
| 10.1 ± 0.2 | M |
| 4.76 ± 0.1 | W |
| 4.29 ± 0.08 | VS |
| 3.98 ± 0.08 | M |
| 3.87 ± 0.07 | VS |
| 3.49 ± 0.07 | W |
| 3.38 ± 0.07 | M |
| 3.20 ± 0.06 | W |
| 3.05 ± 0.05 | W |
| 2.54 ± 0.03 | W |

These values were determined by standard technique. The radiation was the K-alpha doublet of copper, and a diffractometer equipped with a scintillation counter and a strip chart pen recorder was used. The peak heights, I, and the positions as a function of two times theta, where theta is the Bragg angle, were read from the spectrometer chart. From these, the relative intensities, 100 $I/I_o$ where $I_o$ is the intensity of the strongest line or peak, and d (obs.), the interplanar spacing in Angstrom units (Å) corresponding to the recorded lines, were calculated. In Table 1 the relative intensities are given in terms of the symbols W=weak, M=medium, VS=very strong. Ion exchange of the sodium ions with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The term "aromatic compound" as used herein is to be understood in accordance with its art-recognized scope which includes substituted and unsubstituted mono- and polynuclear compounds which must possess at least one hydrogen atom directly bonded to the aromatic nucleus such as condensed or non-condensed aromatic nucleus.

Suitable unsubstituted aromatic compound includes benzene and naphthalene.

Suitable substituted aromatic compounds include toluene, xylene, ethylbenzene, iso-propylbenzene, n-propylbenzene, n-butylbenzene, iso-butylbenzene, tert-butylbenzene, biphenyl, phenol, and cresol.

Styrene derivatives generally include styrene, α-methylstyrene and vinyltoluene. Among the styrene derivatives, a suitable one is styrene.

When styrene is reacted with, for example, benzene, toluene or xylene according to the method of the present invention, 1,1-diaryl-ethane such as 1,1-diphenyl-ethane, 1-phenyl-1-tolyl-ethane, or 1-phenyl-1-xylyl-ethane is obtained, respectively, as an aralkylation product.

Aralkylation conditions include a temperature of between 120° C. and 300° C., preferably 150° C. to 250° C. It is necessary that the reaction pressure be set at a value at which the reaction system can be maintained in a liquid phase at the reaction temperature. The reaction pressure depends upon a reaction temperature and the composition of reactants, in which the pressure is generally preferable in the range of 0.1 to 5 MPa. Even when the reaction pressure is higher than the above range, the reaction can be done without difficulty, however, when the reaction pressure is too high, it is not desirable because it brings about the increase in equipment cost.

The reaction can be carried out in any of known reactors usually employed for aralkylation.

The reactors may be any of batchwise apparatus and continuous apparatus. When a batchwise reactor is employed, it is desirable to use a reactor of perfectly mixing type.

When a continuous flow type reactor is used, the space velocity can be from 0.1 to 100 (hr$^{-1}$) WHSV, preferably 0.2 to 50 (hr$^{-1}$) WHSV. A part of the reaction product thus obtained may be circulated, if necessary.

By distilling the reaction product, the arylalkanes are obtained.

In the following, the present invention will be described in more detail with reference to examples.

EXAMPLE (Catalysts)

Catalyst A

Crystalline ZSM-12 zeolite was synthesized from a reaction mixture comprising tetraethylammonium bromide, a precipitated silica as the silica source, aluminum sulfate as the alumina source, sodium hydroxide, water and a small amount of ZSM-12 crystals as seeds. The mixture had a charge silica to alumina ratio of approximately 260 to 1 and a composition, in weight percent, as follows:

TABLE 2

| Component | Wt. % |
| --- | --- |
| Water | 56.73 |
| 50% NaOH Solution | 2.83 |
| 50% TEABr Solution | 24.56 |
| HiSil 233 Silica (precipitated silica) | 15.06 |
| ZSM-12 Seeds | 0.34 |
| 47% Aluminum Sulfate | 0.48 |

The reaction mixture was placed in a crystallizer where it was heated to 138° C., with continuous mixing until crystallization was complete. The product was identified as crystalline ZSM-12 by x-ray analysis.

This mixture was then filtered and dried to form a drycake. The drycake was mixed with water and a pseudo-boehmite alumina to form an extrudable paste that comprised 65% ZSM-12 and 35% alumina on an anhydrous basis. The paste was extruded into 1/16" cylindrical extrudates, which were then dried and nitrogen calcined at 538° C. The material was then ammonium nitrate exchanged, water washed and finally air calcined at 538° C. to remove any residual carbon on the catalyst. The Alpha Value of this material was measured to be 36.

A portion of the above extrudate product was crushed and fine particles in the size range of 0.35–0.84 mm were collected and calcined at 500° C. for 3 hours in air to obtain Catalyst A.

Catalyst B

β-Zeolite made by Uetikon Co. (trade name: ZEOCAT PB-H 1/16) was crushed and fine particles in the range of 0.35–0.84 mm in particle size were taken and calcined at 500° C. for 3 hours in the air to obtain Catalyst B.

Catalyst C

MCM-22 (trade name, made by ExxonMobil Chemical Company) was crushed and fine particles in the range of 0.35–0.84 mm in particle size were taken and calcined at 500° C. for 3 hours in the air to obtain Catalyst C.

Example 1 and Comparative Examples 1 and 2

A continuous flow type reactor A and a reactant mixture of cumene and styrene in a molar ratio of 10:1 were used. Continuous reaction was carried out under the conditions of: feed rate: 10 g/hr, circulation: 500 g/hr, and pressure: 1 MPa. Concerning the respective catalysts, the selectivity for diarylalkane was compared by changing the reaction temperatures under the condition that the conversion rate of styrene exceeded 99%.

By the way, in the case that catalysts are different in catalytic activity, simple comparison is sometimes difficult because optimum reaction conditions are different markedly. So that, in these examples and comparative examples, comparative tests were done under the conditions that conversion rates of styrene were roughly the same (but reaction temperatures were different).

Catalyst A was used in Example 1, Catalyst B was used in Comparative Example 1 and Catalyst C was used in Comparative Example 2, respectively.

The results of tests are shown in the following Table 3. The conversion rate of styrene and selectivity for diarylethane were calculated with the following equation on the weight percentages of the respective components obtained by gas chromatographic analysis.

TABLE 3

| Example | Example 1 | Comp. Exam. 1 | Comp. Exam. 2 |
| --- | --- | --- | --- |
| Catalyst | Catalyst A | Catalyst B | Catalyst C |
| WHSV (h$^{-1}$) | 5 | 5 | 5 |
| Reaction Temp. (° C.) | 180 | 180 | 170 |
| Conversion Rate of Styrene (%) | 99.9 | 99.5 | 99.5 |
| Selectivity for Diarylethane (%) | 91.3 | 65.2 | 71.6 |

$$\text{Conversion rate of styrene} = \frac{(\text{Wt \% of styrene in Feed 1}) - (\text{Wt \% of styrene in Reaction Product 2})}{(\text{Wt \% of styrene in Feed 1})}$$

$$\text{Selectivity for diarylethane} = \frac{(\text{Wt \% of diarylethane in Reaction Product 2}) \div (\text{Molecular weight of diarylethane})}{[(\text{Wt \% of styrene in Feed 1}) - (\text{Wt \% of styrene in Reaction Product 2})] \div (\text{Mol. wt of styrene})}$$

Example 2 and Comparative Example 3

The reactor A and a reactant mixture of benzene and styrene in a molar ratio of 10:1 were used. Continuous reaction was carried out under the conditions of: feed rate: 10 g/hr, circulation: 500 g/hr, and pressure: 2 MPa.

Concerning the two kinds of catalysts, the selectivity for diarylalkane was compared by changing the reaction temperatures under the condition that the conversion rate of styrene was about 95%. By the way, in these examples, the conversion rate of styrene was adjusted to about 95% because, when the conversion rate is too high, the deterioration of reaction products is liable to occur.

Catalyst A was used in Example 2 and Catalyst B was used in Comparative Example 3, respectively. The quantity of filled catalyst in both cases was 2 g. The results of tests are shown in the following Table 4.

TABLE 4

| Example | Example 2 | Comp. Exam. 3 |
| --- | --- | --- |
| Catalyst | Catalyst A | Catalyst B |
| WHSV ($h^{-1}$) | 5 | 5 |
| Conversion Rate of Styrene (%) | 94.7 | 94.5 |
| Selectivity for Diarylethane (%) | 59.1 | 9.8 |

Example 3

The reactor A fed with 2 g of catalyst A and a reactant mixture of cumene and styrene in a molar ratio of 10:1 were used. Continuous reaction was carried out under the conditions of: feed rate: 10 g/hr, circulation: 500 g/hr, temperature: 190–220° C., and pressure: 1 MPa. The results of tests are shown in the following Table 5.

TABLE 5

| Throughput [Feed (wt)/Catalyst (wt)] | 1190 | 2030 | 3710 | 5030 |
| --- | --- | --- | --- | --- |
| WHSV ($h^{-1}$) | 5 | 5 | 5 | 5 |
| Reaction Temp. (° C.) | 190 | 200 | 210 | 220 |
| Conversion Rate of Styrene (%) | 99.7 | 99.7 | 99.5 | 99.2 |
| Selectivity for Diarylethane (%) | 91.6 | 91.9 | 91.2 | 89.1 |

What is claimed is:

1. A method for producing a diarylethane by aralkylating an aromatic hydrocarbon selected from the group consisting of benzine and cumene with styrene under a liquid phase condition in the presence of a synthetic porous crystalline material having the structure of ZSM-12, wherein the molar ratio of the aromatic hydrocarbon to the styrene derivative is at least 10:1.

2. The method of claim 1 wherein the molar ratio of aromatic hydrocarbon to styrene is 10:1.

3. The method according to claim 1 wherein the aromatic hydrocarbon and styrene derivative are reacted in a continuous reactor.

* * * * *